United States Patent [19]

Hofstetter et al.

[11] Patent Number: 5,518,997
[45] Date of Patent: May 21, 1996

[54] METHOD OF PREPARING STABLE LIQUID PERFUME MATERIAL MIXTURES WITH A HIGH SOLIDS CONTENT

[75] Inventors: Otto Hofstetter, Birkenau, Germany; Gerhard Oswald, Alzey, both of Germany

[73] Assignee: Procter and Gamble Co., Cincinnati, Ohio

[21] Appl. No.: 256,293

[22] PCT Filed: Jan. 7, 1993

[86] PCT No.: PCT/EP93/00014

§ 371 Date: Sep. 12, 1994

§ 102(e) Date: Sep. 12, 1994

[87] PCT Pub. No.: WO93/13749

PCT Pub. Date: Jul. 22, 1993

[30] Foreign Application Priority Data

Jan. 10, 1992 [DE] Germany ............... 42 00 433.0

[51] Int. Cl.$^6$ ..................................... A61K 7/46
[52] U.S. Cl. ................. 512/2; 512/17; 512/21
[58] Field of Search ..................... 512/2, 17, 21

[56] References Cited

U.S. PATENT DOCUMENTS

| | | | |
|---|---|---|---|
| 2,875,131 | 2/1959 | Carpenter et al. | 512/21 |
| 3,548,006 | 12/1970 | Siriabine | 512/2 |
| 4,650,603 | 3/1987 | Sprecker | 512/2 |

FOREIGN PATENT DOCUMENTS

| | | | |
|---|---|---|---|
| 3922389 | 1/1991 | Germany | 512/2 |

OTHER PUBLICATIONS

Arctander, "Perfume & Flavor Chemicals", (1969) pp. 13, 41, 340, 496, 1654.

Primary Examiner—James H. Reamer
Attorney, Agent, or Firm—Foley & Lardner

[57] ABSTRACT

Method of preparing homogeneous mixtures of liquid and/or solid perfume materials by mixing the components and liquefying the mixture, in which a binary or ternary eutectic premix which is liquid at room temperature and contains 10–90% of the individual substances in the case of binary mixtures and 10–70% in the case of ternary mixtures is formed from a) the solid 6-acetyl-1,1,3,4,4,6-hexamethyltetrahydronaphthalene,
b) the solid or oily α,n-hexylcinnamaldehyde,
c) the oily p-tert-butyl-α-methylhydrocinnamaldehyde,
d) the solid p-methoxyacetophenone and
e) the solid benzyl o-hydroxybenzoate, and the remaining solid and liquid products are introduced into this mixture simultaneously or in a sequence which is freely chosen for the particular mixture and is independent of the chemical and physical nature of the substances, and the binary and ternary eutectic premixes prepared in this manner.

23 Claims, No Drawings

METHOD OF PREPARING STABLE LIQUID PERFUME MATERIAL MIXTURES WITH A HIGH SOLIDS CONTENT

This application is a 371 of PCT/EP 93/00014, filed Jan. 7, 1993.

The invention relates to a novel method of preparing homogeneous liquid mixtures of solid perfume materials and the use of these mixtures for preparing solvent-free ready-made perfume formulations.

For application reasons (e.g. stability, odor intensity or substantivity), solids are being increasingly used in the modern perfume industry. These substances are indispensable in particular for perfumes for detergents and softeners, since these products are subjected to considerable stresses during preparation, in the market and subsequently during processing. The fragrance of these products is not only of decisive importance in decisions for or against the purchase of a certain product but also accompanies the product from production through storage to use. In addition, the laundry which has been washed or treated with a softener must have a pleasant odor—even after weeks of storage—in order to meet the high quality expectations of the buyer of a branded article.

The problem of these extreme quality requirements with regard to a modern ready-made perfume is illustrated by the fact that about 99.9% of the industrial perfume used "disappears" in the wastewater in the washing or softening process, while only about 0.1% is absorbed by the washed laundry.

For mixing perfume materials, the chemically stable, liquid components are usually initially introduced, as a rule with the addition of further solvents, such as dipropylene glycol (DPG) and diethyl phthalate (DEP) and the like, and the solid components are added gradually with vigorous stirring, the mixture being heated externally or by means of internal heating coils until the solids melt or go into solution. Since the heating surfaces have to be heated to relatively high temperatures in order to achieve sufficient heat transport, a certain amount of damage occurs at these heating surfaces as a result of overheating, particularly in the case of sensitive substances. Moreover, the vigorous mixing results in greater contact with air, so that it is necessary to work under an expensive inert gas atmosphere in order to avoid damage by oxidation.

After dissolution of the solids, the mixture is cooled. Sensitive, readily volatile or chemically unstable materials are then added with gentle stirring, and stirring is continued until the mixture is homogeneous. This method is considerably time-consuming since a disadvantageous solid/liquid mixing ratio is initially present or a time-consuming heating and cooling process is necessary in between and the use of additional solvents not only incurs costs and unnecessarily increases the processing quantities but also additionally pollutes the environment.

DE-A 39 22 389.2 describes a process in which the introduction of the solid materials into the liquid substances is carried out with simultaneous addition of an inert gas to the stirring zone, with the result that the damage which occurs due to overheating and mechanical stressing of the sensitive materials is completely avoided.

However, it proves to be disadvantageous that the proportion of solid substances in conventional perfume formulations is in fact comparatively high and that such substances may be difficult to meter and convey and furthermore, as powders, occupy large volumes, giving rise to transport and storage problems. As a remedy, such substances are in some cases therefore dissolved in suitable solvents and thus converted into the liquid state, with the result that metering and handling are simplified. However, this has the disadvantage that the total amount is greatly increased due to the amounts of solvent, with the result that transport and storage once again become expensive and in addition solvents are introduced into the formulation, which not only constitute a cost factor themselves but are also to be classified as causing environmental pollution.

The above-mentioned solid contents of 20-60% of the total perfume mixture are composed of, in each case, about 20 different materials, which in turn are selected from about 100 conventional materials, depending on the desired fragrance note. 5 of these substances, namely 6-acetyl-1,1,3,4,4,6-hexamethyltetrahydronaphthalene, α,n-hexylcinnamaldehyde, p-tert-butylmethylhydrocinnamaldehyde, p-methoxyacetophenone and benzyl o-hydroxybenzoate, which occur in virtually all formulations, although in different amounts, account for as much as over 70% of the total amount. Together with the 10 next most frequent substances, the amount increases as much as over 90%. The next 10 substances in terms of quantity increase the amount to over 95%. All other substances are present only in amounts of less than 0.5%, so that admixing them presents no problems.

In order to avoid the disadvantages in the processing of solids, it is therefore the object to convert these substances or at least the main components into the liquid state and to provide them in this form, even after prolonged storage, for the final mixing process.

Relatively long-term storage above the particular melting point is out of the question not only because of the costs but in particular for stability and quality reasons. Dissolution in solvents having a "neutral odor", such as diethyl phthalate (DEP) or dibutyl glycol, dipropylene glycol (DPG) and similar solvents, which is practiced in some cases for components present in insignificant amounts, is of course out of the question for products present in major amounts, because as a result too large an amount of solvents which pollute the environment and harm the product are introduced into the formulation.

Prior dissolution in the "liquid" components of the formulations is not possible because, if they occur in relatively large amounts, for example phenylethyl alcohol, they are poor solvents, or they are used only in relatively small ratios which change for the different formulations, so that prior dissolution is not suitable owing to the associated storage and logistic problems.

Surprisingly, it has now been found that the above-mentioned solid or viscous main products can be combined to give binary and ternary mixtures (fragrance building blocks) which have a low viscosity not only at room temperature but, in some cases, also down to 0° C. or −20° C., and that virtually all commonly used industrial perfume formulations can be prepared without the addition of solvents by combining these fragrance building blocks in suitable ratios.

These liquid mixtures, which are still liquid at temperatures of 30°–80° C. below the melting point of the components, i.e. in some cases at −20° to 0° C., are referred to below as "eutectic mixtures" in order to indicate the unexpectedly low freezing point compared with the individual components. Whether particular solid phases mix with one another or not, i.e. whether true eutectic mixtures are present, was not investigated or taken into account.

Properties of the materials 1. 6-Acetyl-1,1,3,4,4,6-hexamethyltetrahydronaphthalene White crystalline powder, melting point (according to purity) 55°–60° C., commercial purity 95–99.8%, binds foreign odors very readily, high substantivity, relatively poorly soluble in liquid perfume materials, readily soluble in diethyl phthalate and alcohol, musk odor.

2. α-Hexylcinnamic aldehyde (HCA)

Solid at 10°–23° C. At higher temperature, yellowish, oily liquid which has a high tendency to oxidation (cinnamic acid). Dissolves readily in diethyl phthalates and dipropylene glycol, floral, fruity note.

3. Benzyl salicylate (BSA)

Crystalline mass which melts at about 25°–30° C. to give a colorless oily substance. Soluble in diethyl phthalate, poorly soluble in dipropylene glycol. Sweet-floral, slightly balsamic odor of low intensity.

4. p-Methoxyacetophenone or methyl 4-methoxyphenyl ketone (PMA)

Colorless crystals which tend to agglomerate. Melting point 36°–40° C. Typically floral-sensual intense odor, poorly soluble in liquid perfume materials, dipropylene glycol, readily soluble in diethyl phthalates and alcohol.

5. p-tert-Butyl-α-methylhydrocinnic aldehyde (PTB)

Colorless, oily liquid, dissolves in alcohol and other perfume oils and diethyl phthalates. Fresh aldehydic floral odor, very sensitive to oxidation, solidifies to the solid carboxylic acid (cinnamic acid derivative), risk of autoxidation and spontaneous ignition, is eliminated in a mixture with other suitable perfume materials.

The short designations appended above in parentheses are used in the text below.

As binary or multi-substance mixtures, the mixtures of the stated 5 individual materials, proposed according to the invention, exhibit, in wide mixing ratios, a surprisingly pronounced melting point depression in conjunction with excellent thermal stability and chemical stability to oxidation and polymerization. In all cases, stable liquids are formed by mixing two or more of the stated substances in the specified ratios. These liquids can be metered without problems via pumps and valves as "fragrance building blocks" with the other liquid materials without further pretreatment at temperatures of 10°–20° and can be further processed in simple mixers to give ready-made perfume formulations.

In some cases, surprising "superstability" was obtained since some mixtures still remain liquid (of low viscosity to medium viscosity) even on prolonged storage in temperature ranges from minus 18° to minus 20° C. Even the addition of seed crystals does not cause these mixtures to crystallize. The individual results obtained are shown in the Tables below, the following classification being used:

1= Solidifies directly after cooling
2= Solidifies completely after one day
3= Solidifies partly after one day
4= Solidifies completely after 3 days
5= Solidifies partly after 3 days
6= Does not solidify after 3 days In some cases, the viscosity was measured at 20° C. Corresponding values in mPa.s are likewise shown in the Tables below.

Mixture of 6-acetyl-1,1,3,4,4,6-hexamethyltetrahydronaphthalene (AHN), hexylcinnamaldehyde (HCA) and p-tert-butyl-α-methylhydrocinnamaldehyde (PTB)

| AHN | Parts HCA | PTB | Visc. | −20° C. | 0° C. | +10° C. | +20° C. |
|---|---|---|---|---|---|---|---|
| 40 | 10 | 50 |    | 5 | 5 | 6 | 6 |
| 40 | 20 | 40 |    | 6 | 6 | 6 | 6 |
| 40 | 30 | 30 | 32 | 6 | 6 | 6 | 6 |
| 40 | 40 | 20 |    | 6 | 6 | 6 | 6 |
| 40 | 50 | 10 |    | 4 | 4 | 6 | 6 |
| 50 | 5  | 45 |    | 4 | 4 | 6 | 6 |
| 50 | 15 | 35 | 42 | 6 | 6 | 6 | 6 |
| 50 | 25 | 25 | 42 | 6 | 6 | 6 | 6 |
| 50 | 35 | 15 |    | 4 | 4 | 5 | 6 |
| 50 | 45 | 5  |    | 4 | 4 | 5 | 6 |
| 60 | 10 | 30 |    | 6 | 6 | 6 | 6 |
| 60 | 20 | 20 | 53 | 6 | 6 | 6 | 6 |
| 60 | 30 | 10 |    | 4 | 5 | 5 | 6 |

Mixture of 6-acetyl-1,1,3,4,4,6-hexamethyltetrahydronaphthalene (AHN) and p-methoxyacetophenone (PMA)

| AHN | Parts PMA | Visc. | −20° C. | 0° C. | +10° C. | +20° C. |
|---|---|---|---|---|---|---|
| 25 | 75 |    | 1 | 2 | 2 | 5 |
| 50 | 50 | 27 | 1 | 2 | 3 | 6 |
| 75 | 25 |    | 1 | 2 | 2 | 5 |

Mixture of 6-acetyl-1,1,3,4,4,6-hexamethyltetrahydronaphthalene (AHN) and hexylcinnamaldehyde (HCA)

| AHM [sic] | Parts HCA | Visc. | −20° C. | 0° C. | +10° C. | +20° C. |
|---|---|---|---|---|---|---|
| 90 | 10 |    | 1 | 1 | 1 | 1 |
| 80 | 20 |    | 1 | 1 | 4 | 4 |
| 70 | 30 |    | 1 | 4 | 6 | 6 |
| 60 | 40 | 30 | 1 | 5 | 6 | 6 |
| 50 | 50 | 40 | 1 | 5 | 6 | 6 |

| | | | | | | |
|---|---|---|---|---|---|---|
| 40 | 60 | | 2 | 6 | 6 | 6 |
| 30 | 70 | | 5 | 5 | 6 | 6 |
| 20 | 80 | 100 | 1 | 5 | 5 | 6 |
| 10 | 90 | | 1 | 4 | 5 | 6 |

Mixture of 6-acetyl-1,1,3,4,4,6-hexamethyltetrahydro-naphthalene (AHN) and benzyl salicylate (BSA)

| AHN | Parts BSA | Visc. | −20° C. | 0° C. | +10° C. | +20° C. |
|---|---|---|---|---|---|---|
| 90 | 10 | | 1 | 1 | 1 | 1 |
| 80 | 20 | | 1 | 1 | 1 | 2 |
| 70 | 30 | | 2 | 2 | 4 | 5 |
| 60 | 40 | | 4 | 4 | 5 | 5 |
| 50 | 50 | | 4 | 4 | 5 | 6 |
| 40 | 60 | 40 | 5 | 5 | 6 | 6 |
| 30 | 70 | 32 | 5 | 6 | 6 | 6 |
| 20 | 80 | | 5 | 5 | 6 | 6 |
| 10 | 90 | | 2 | 4 | 4 | 6 |

Mixture of hexylcinnamaldehyde (HCA) and benzyl salicylate (BSA)

| HCA | Parts BSA | Visc. | −20° C. | 0° C. | +10° C. | +20° C. |
|---|---|---|---|---|---|---|
| 90 | 10 | | 2 | 4 | 5 | 6 |
| 80 | 20 | | 2 | 4 | 5 | 6 |
| 70 | 30 | | 4 | 5 | 6 | 6 |
| 60 | 40 | | 4 | 5 | 6 | 6 |
| 50 | 50 | 20 | 5 | 6 | 6 | 6 |
| 40 | 60 | 20 | 4 | 6 | 6 | 6 |
| 30 | 70 | | 2 | 5 | 5 | 6 |
| 20 | 80 | | 2 | 5 | 5 | 6 |
| 10 | 90 | | 2 | 4 | 5 | 6 |

Mixture of benzyl salicylate (BSA) and para-methoxyacetophenone (PMA)

| BSA | Parts PMA | Visc. | −20° C. | 0° C. | +10° C. | +20° C. |
|---|---|---|---|---|---|---|
| 20 | 80 | | 2 | 2 | 4 | 4 |
| 50 | 50 | 17 | 2 | 5 | 6 | 6 |
| 66.6 | 33.3 | | 4 | 6 | 6 | 6 |
| 80 | 20 | | 2 | 6 | 6 | 6 |

Mixture of hexylcinnamaldehyde (HCA) and para-methoxyacetophenone (PMA)

| HCA | Parts PMA | Visc. | −20° C. | 0° C. | +10° C. | +20° C. |
|---|---|---|---|---|---|---|
| 80 | 20 | | 4 | 6 | 6 | 6 |
| 60 | 40 | 15 | 4 | 5 | 6 | 6 |
| 40 | 60 | | 4 | 3 | 5 | 5 |
| 20 | 80 | | 1 | 2 | 2 | 4 |

Mixture of 6-acetyl-1,1,3,4,4,6-hexamethyltetrahydro-naphthalene (AHN), hexylcinnamaldehyde (HCA) and benzyl salicylate (BSA)

| AHN | Parts HCA | BSA | Visc. | −20° C. | 0° C. | +10° C. | +20° C. |
|---|---|---|---|---|---|---|---|
| 40 | 10 | 50 | | 4 | 4 | 5 | 6 |
| 40 | 20 | 40 | | 4 | 5 | 6 | 6 |
| 40 | 30 | 30 | 30 | 6 | 6 | 6 | 6 |
| 40 | 40 | 20 | | 6 | 6 | 6 | 6 |
| 40 | 50 | 10 | 30 | 6 | 6 | 6 | 6 |
| 50 | 5 | 45 | | 4 | 4 | 5 | 6 |
| 50 | 15 | 35 | 45 | 4 | 4 | 5 | 6 |
| 50 | 25 | 25 | | 4 | 5 | 6 | 6 |
| 50 | 35 | 15 | 40 | 6 | 6 | 6 | 6 |
| 50 | 45 | 5 | | 6 | 6 | 6 | 6 |
| 60 | 10 | 30 | | 2 | 4 | 5 | 6 |
| 60 | 20 | 20 | | 2 | 4 | 5 | 6 |
| 60 | 30 | 10 | | 2 | 4 | 5 | 6 |

Preparation of the eutectic mixtures

The preparation of the material mixtures which are stable in liquid form presents no problems at all. Having one or more of the components present in liquid form and directly combining them in the intended ratio has proved particularly advantageous here. Since all individual components are in liquid form directly after their synthesis, the preparation of the eutectic mixtures directly by raw material producers is particularly energy-saving and simple.

However, it is also possible for the mixtures to be prepared by the users themselves, by initially introducing premelted stable individual components and mixing them in the intended ratio with crystalline materials.

The addition of the liquid fragrance building blocks to the remaining formula is carried out without further pretreatment at room temperature by simply pumping in or via metering valves controlled by a process computer. Parts of the perfume mixing process which were previously impossible to automate for technical reasons can thus be automated.

The homogeneous final mixing is carried out in all cases after the addition by a short stirring process or by circulation/pumping.

The odorless traditional solvents (diethyl phthalate, dipropylene glycol, etc.) used in the traditional perfume process for predissolving the large amounts of solid prove to be superfluous if preliquefied solid mixtures are used. Since in this case the process is carried out at room temperature, the components of the perfume formula which are sensitive to oxidation or polymerization or are readily volatile can be added in any order which can be freely chosen.

Since only liquids which can be homogenized without any problems at all are used in the method proposed according to the invention, considerable increases in capacity compared with traditional perfume mixing processes are permitted.

The liquid eutectic mixtures proposed according to the invention and comprising the stated individual components can be used as fragrance building blocks in the following variations.

| BSA | HCA | PTB | AHC | PMA |
|---|---|---|---|---|
| sweet floral, balsamic | sweet floral, slightly fruity | sweet floral, aldehydic green | musk | sweet floral, woody, sensual | fresh, floral, fruity, aldehydic green fresh, floral, aldehydic green musk note sweet, floral, balsamic musk note fresh, floral, sweet musk note with woody sensual background rich, floral, aldehydic fresh musk note with balsamic/ woody sensual background.

The above fragrance building blocks may be regarded as basic building blocks of a modern industrial perfume formula which, when used in the very wide range of variations, account for about 20–50% of the total formula or 70–90% of solids. All formula variations tested to date were liquid at room temperature.

The preparation of further successful fragrance building blocks based on the proposed basic building block is possible by adding further components as follows, and is possible in all variations.

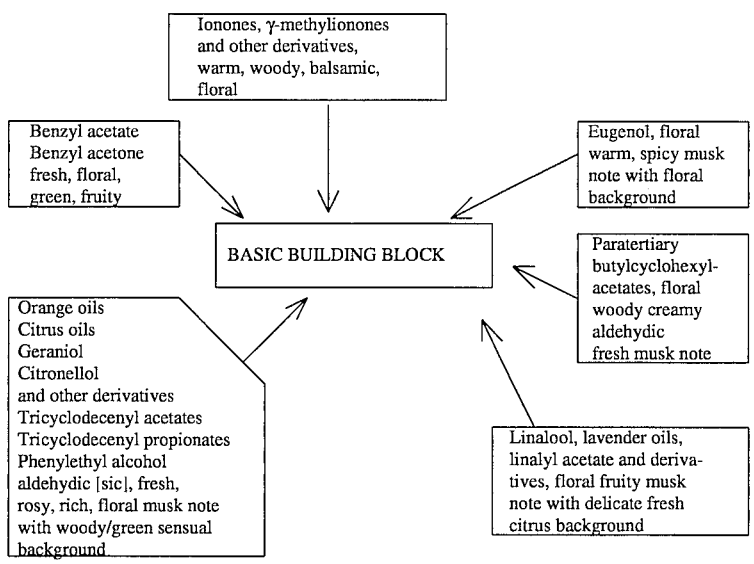

The proportion of these fragrance building blocks composed of a few basic components in all current industrial perfume formulas is between 40 and 90%.

The other substances which are either liquid or are solid and to be used in small amounts can thus be mixed without problems.

The ready-made perfume mixtures prepared by the method proposed according to the invention surprisingly prove to be "superstable at freezing points of 0° to minus 20° C." even without solvent components. The expensive storage of ready-made perfumes in heated storage rooms can thus be avoided in the future without any quality risk.

We claim:

1. A method of preparing a homogenous perfume mixture, comprising mixing a binary or ternary eutectic premix which is liquid at room temperature with additional perfume components to form the homogenous mixture, wherein the binary eutectic premix consists essentially of two components selected from the group consisting of:
   a) 6-acetyl-1,1,3,4,4,6-hexamethyltetrahydronaphthalene,
   b) α,n-hexylcinnamaldehyde,
   c) p-tert-butyl-α-methylhydrocinnamaldehyde,
   d) p-methoxyacetophenone, and
   e) benzyl o-hydroxybenzoate, and the binary eutectic premix is present in an amount of 10–90%, and wherein the ternary eutectic premix consists essentially of three components selected from the group consisting of:
   a) 6-acetyl-1,1,3,4,4,6-hexamethyltetrahydronaphthalene,
   b) α,n-hexylcinnamaldehyde,
   c) p-tert-butyl-α-methylhydrocinnamaldehyde,
   d) p-methoxyacetophenone, and
   e) benzyl o-hydroxybenzoate, and the ternary eutectic premix is present in an amount of 10–70%.

2. A method of preparing a homogenous perfume mixture, according to claim 1, wherein the additional perfume components comprise solid materials and the mixture is further heated to liquify or dissolve the solid material.

3. A method of preparing a homogenous perfume mixture according to claim 2, wherein the mixture is maintained at a temperature between the melting point of the eutectic premix and the melting point of the solid material.

4. A method of preparing a homogenous perfume mixture according to claim 2, wherein the heat required to liquify or dissolve the solid material is supplied by one or more of an ultrasonic or microwave generator.

5. A method of preparing a homogenous perfume mixture according to claim 1, wherein the binary or ternary eutectic premix are fragrance building blocks for a desired fragrance formulation, and the mixing includes combining two or more of the binary or ternary eutectic premixes of different compositions to produce the desired formulation.

6. A method of preparing a homogenous perfume mixture according to claim 5, wherein additional perfume materials are combined with the fragrance building blocks to modify the fragrance formulation.

7. A method of preparing a homogenous perfume mixture according to claim 1, wherein no solvents are added in the mixing, and the addition of the binary or ternary eutectic premix and the additional perfume components to the mixture is computer-controlled.

8. A method of preparing a binary or ternary eutectic perfume premix consisting essentially of combining two or more components selected from the group consisting of:
   a) 6-acetyl-1,1,3,4,4,6-hexamethyltetrahydronaphthalene,
   b) α,n-hexylcinnamaldehyde,
   c) p-tert-butyl-α-methylhydrocinnamaldehyde,
   d) p-methoxyacetophenone, and
   e) benzyl o-hydroxybenzoate, to thereby form the premix.

9. A method according to claim 8, wherein no solvents are added to the premix.

10. A binary or ternary eutectic perfume premix which consists essentially of two or more components selected from the group consisting of:
    a) 6-acetyl-1,1,3,4,4,6-hexamethyltetrahydronaphthalene,
    b) α,n-hexylcinnamaldehyde,
    c) p-tert-butyl-α-methylhydrocinnamaldehyde,
    d) p-methoxyacetophenone, and
    e) benzyl o-hydroxybenzoate.

11. A premix according to claim 10, wherein the premix is a binary mixture of two of the components.

12. A premix according to claim 10, wherein the premix is a ternary mixture of three of the components.

13. A premix according to claim 10, wherein the components comprise 6-acetyl-1,1,3,4,4,6-hexamethyltetrahydronaphthalene and α,n-hexylcinnamaldehyde.

14. A premix according to claim 10, wherein the components comprise 6-acetyl-1,1,3,4,4,6-hexamethyltetrahydronaphthalene and p-tert-butyl-α-methylhydrocinnamaldehyde.

15. A premix according to claim 10, wherein the components comprise 6-acetyl-1,1,3,4,4,6-hexamethyltetrahydronaphthalene and p-methoxyacetophenone.

16. A premix according to claim 10, wherein the components comprise 6-acetyl-1,1,3,4,4,6-hexylmethyltetrahydronaphthalene and benzyl o-hydroxy-benzoate.

17. A premix according to claim 10, wherein the components comprise α,n-hexylcinnamaldehyde and p-tert-butyl-α-methylhydrocinnamaldehyde.

18. A premix according to claim 10, wherein the components comprise α,n-hexylcinnamaldehyde and p-methoxyacetophenone.

19. A premix according to claim 10, wherein the components comprise α,n-hexylcinnamaldehyde and benzyl o-hydroxybenzoate.

20. A premix according to claim 10, wherein the components comprise p-tert-butyl-α-methyl-hydrocinnamaldehyde and p-methoxyacetophenone.

21. A premix according to claim 10, wherein the components comprise p-tert-butyl-α-methyl-hydrocinnamaldehyde and benzyl o-hydroxybenzoate.

22. A premix according to claim 10, wherein the components comprise p-methoxyacetophenone and benzyl o-hydroxybenzoate.

23. A premix according to claim 10, wherein the components comprise 6-acetyl-1,1,3,4,4,6-hexamethyltetrahydronaphthalene, α-hexylcinnamaldehyde and benzyl salicylate.

* * * * *